United States Patent [19]

Pillari

[11] Patent Number: 4,834,708
[45] Date of Patent: May 30, 1989

[54] PUNCTURE NEEDLE ASSEMBLY

[76] Inventor: George Pillari, P.O. Box 465, Parish Dr., Locust Valley, N.Y. 11560

[21] Appl. No.: 32,357

[22] Filed: Mar. 31, 1987

[51] Int. Cl.⁴ .............................................. A61M 5/18
[52] U.S. Cl. .................................................. 604/165
[58] Field of Search ........ 604/165, 164, 162, 116–117, 604/177, 281

[56] References Cited

U.S. PATENT DOCUMENTS

| | | |
|---|---|---|
| D. 258 | 2/1981 | De Frank . |
| 2,725,058 | 11/1955 | Rathkey ................................ 604/177 |
| 3,399,674 | 9/1968 | Pannier et al. . |
| 3,463,152 | 8/1969 | Sorenson ............................. 604/162 |
| 3,506,007 | 4/1970 | Henkin . |
| 3,537,451 | 11/1970 | Beck .................................... 604/165 |
| 3,572,334 | 3/1971 | Petterson . |
| 3,584,625 | 6/1971 | Swick . |
| 3,589,361 | 6/1971 | Loper ................................... 604/165 |
| 3,595,230 | 7/1971 | Suyeoka . |
| 3,596,658 | 8/1971 | Lange . |
| 3,611,965 | 10/1971 | Lange . |
| 3,670,727 | 6/1972 | Reiterman .......................... 604/177 |
| 3,782,381 | 1/1974 | Winnie . |
| 3,856,009 | 12/1971 | Winnie . |
| 3,906,946 | 9/1975 | Nordström . |
| 4,013,080 | 3/1977 | Froning . |
| 4,015,600 | 4/1977 | Liautaud . |
| 4,037,600 | 7/1977 | Poncy et al. . |
| 4,100,393 | 7/1978 | Luther . |
| 4,192,305 | 3/1980 | Seberg . |
| 4,233,974 | 11/1980 | Desecki et al. ..................... 604/165 |
| 4,326,519 | 4/1982 | D'Alo et al. ........................ 604/165 |
| 4,353,369 | 11/1982 | Muetterties et al. . |
| 4,362,156 | 12/1982 | Feller, Jr. et al. . |
| 4,401,433 | 8/1983 | Luther ................................ 604/281 |
| 4,405,307 | 9/1983 | Taylor . |
| 4,417,886 | 11/1983 | Frankhouser et al. . |
| 4,444,203 | 4/1984 | Engelman . |
| 4,445,893 | 5/1984 | Bodick ............................... 604/165 |
| 4,496,348 | 1/1985 | Genese et al. . |

Primary Examiner—John D. Yasko
Attorney, Agent, or Firm—Bernard, Rothwell & Brown

[57] ABSTRACT

A puncture needle assembly includes a hollow, open-ended stylet with a beveled distal end and an outwardly extending stabilizer fin located at the proximal end of the stylet in line with the beveled end of the stylet. A needle cannula is disposed exteriorly on the stylet for slidably receiving the stylet. The needle cannula releasably interlocks with the stylet, and includes a pair of wings that fold towards each other for gripping the stabilizer fin of the stylet in the interlocked position, with the proximal end of the stylet spaced away from the wing fold portions to facilitate visibility of blood passing from a blood vessel through the stylet out an opening in the proximal end thereof.

16 Claims, 2 Drawing Sheets

PUNCTURE NEEDLE ASSEMBLY

BACKGROUND OF THE INVENTION

1. Field of the Invention

The present invention relates to a puncture needle assembly for providing access to arterial and venous blood vessels.

2. Description of the Background Art

An important aspect of angiography and vascular studies in access to the circulatory system, that is, to blood vessels such as arteries and veins. In such studies, access to the circulation typically involves insertion of a hollow needle into a groin artery, although the needle sometimes is inserted in a blood vessel in the arm.

There have been problems with accurate insertion of previously known puncture needles into arteries of the groin or in the arm because of the awkward positioning required. When a needle is inserted into the blood vessel, the desired procedure is to puncture the front wall of the blood vessel and to stop the needle with the tip of the needle within the blood vessel itself without puncturing the back wall of the blood vessel. Proper positioning of the tip of the needle is determined by blood passing from the artery through the needle and out the back end of the needle. However, previously known puncture needles for accessing blood vessels for angiography and vascular studies frequently must be gripped with the thumb and two fingers. This usually requires that the back end of the needle be covered or concealed by the hand, due to the awakwardness of positioning previously known needles in a blood vessel in the groin area or in an arm. Accordingly, a determination of the proper positioning of the tip of the needle is difficult with prior art puncture needles due to the back end of the needle being covered by the hand.

There remains a need in the art for a puncture needle assembly for gaining access to blood vessels in the groin and the arm during angiography and vascular studies, that does not possess the disadvantages of prior art needles used for such purposes.

SUMMARY OF THE INVENTION

In accordance with the present invention, a puncture needle assembly includes a hollow, open-ended stylet through which liquid may pass. The stylet is beveled at a distal end thereof to form a point on one side of the stylet, and a stylet hub assembly is fixed about a proximal end of the stylet. The stylet hub assembly includes a stabilizer fin extending outwardly from the stylet hub assembly in a plane defined by the longitudinal axis of the stylet and the point of the beveled end of the stylet. The fin extends radially from a side of the stylet that is opposite the end on which the stylet point is located. A needle cannular is disposed exteriorly on the stylet for slidably receiving the stylet. The needle cannula terminates at a proximal end thereof in a cannula hub having a body portion and further including a pair of wings extending outwardly from the cannula body portion. The wings have flexible hinge areas adjacent the cannula body portion that allow the wings to fold towards each other about the cannula axis. The body portion of the cannula hub includes means for interacting with the stylet hub for releasably interlocking the cannula hub and the stylet hub assembly in a selectively locked position to prevent rotation of the stylet within the needle cannula. In the locked position, the beveled distal end of the stylet extends outside a distal end of the needle cannula and the stabilizer fin is disposed between the cannula wings and positioned substantially equidistant from the hinge areas of the cannula wings so that the stabilizer fin can be gripped between the cannula wings when the cannula wings are folded towards each other substantially symmetrically with respect to the plane of the stabilizer fin.

DETAILED DESCRIPTION OF THE PREFERRED EMBODIMENT

Figure 1:
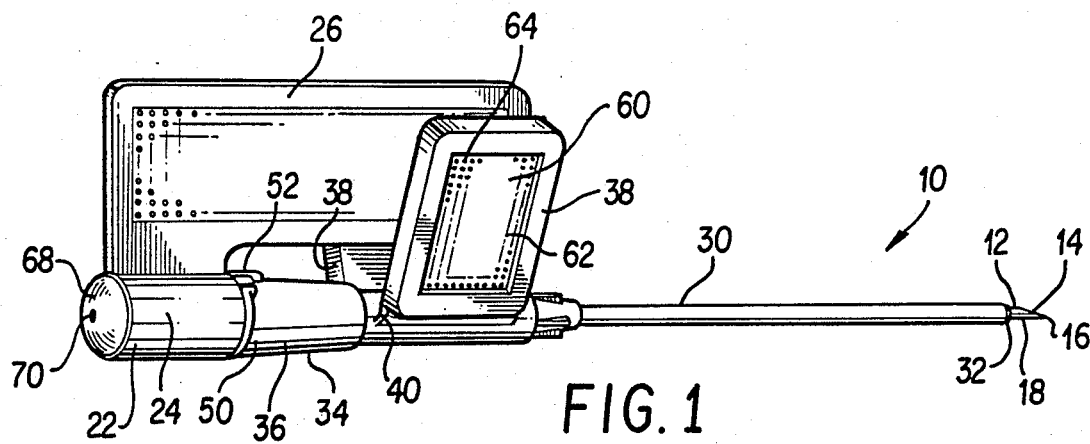
FIG. 1 is a perspective view of an assembled puncture needle assembly according to the invention.

The assembled puncture needle assembly 10 according to the invention shown in FIG. 1 includes a hollow, open-ended stylet 12 through which liquid such as blood may pass. The stylet 12 is beveled at a distal end 14 to form a point 16 on one side 18 of stylet 12.

The hollow stylet needle portion can be, for example, 18 or 19 gauge hollow, surgical stainless steel needle tubing. According to one embodiment, the overall bevel length (dimension C of FIG. 4) of the beveled end 14 of stylet 12 is 0.086±0.009 inch, the bevel including a sharpened edge portion 20 of the tip (dimension B of FIG. 4) that comprises about 40-50% of the overall bevel length (dimension C of FIG. 4). According to this embodiment, level 14 has a bevel angle when viewed end-on of about 110°±5°. See FIG. 5.

Figure 2:
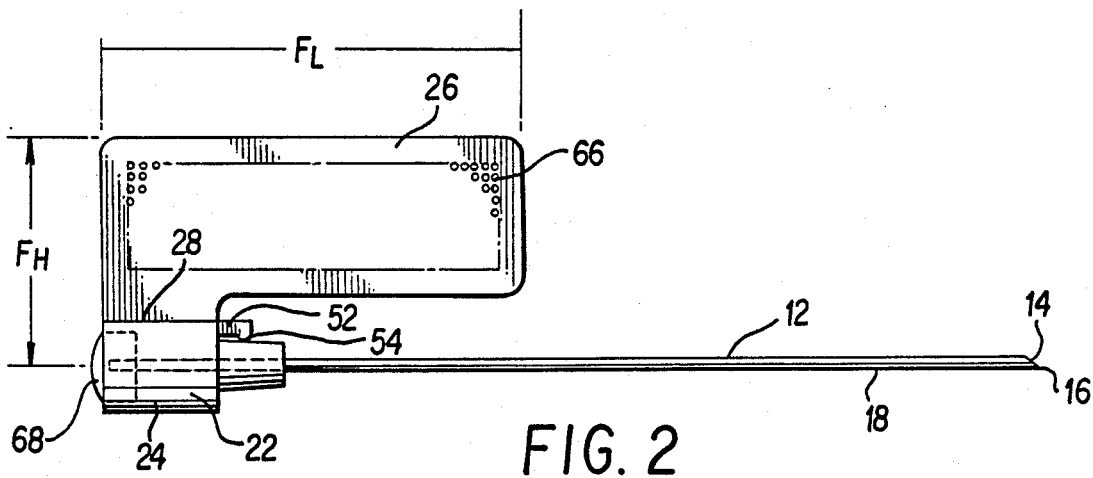
FIG. 2 is a side elevational view of the stylet portion of the puncture needle assembly shown in FIG. 1.
Figure 3:
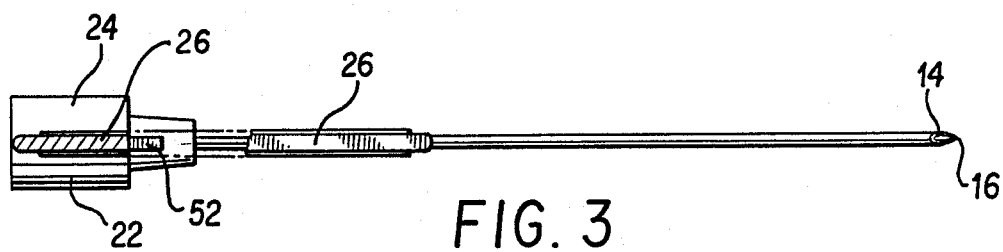
FIG. 3 is a top elevational view of the stylet shown in FIG. 2, with a portion of the stylet fin broken away for clarity.

A stylet hub assembly 22 is fixed about a proximal end of stylet 12. FIGS. 1, 2 and 3. The stylet hub assembly 22 includes a body portion 24 and a rigid stabilizer fin 26 extending outwardly from the body portion 24 of stylet hub assembly 22. Fin 26 is rigidly connected to the body portion 24 of hub assembly 22, and extends in a plane defined by the longitudinal axis of the hollow needle portion of stylet 12 and the point 16 of the beveled end 14 of the stylet, the fin extending radially from a side 28 of the stylet hub assembly 22 that is opposite the side 18 on which the stylet point 16 is located, as clearly shown in FIG. 2.

According to one embodiment, fin 26 is between about 1-2 inches in length (dimension $F_L$ in FIG. 2) preferably about 1-11/32 inches in length. According to this embodiment, the fin extends about ½-1 inch, preferably about ¾ inch, outwardly from the axis of stylet 12 (dimension $F_H$ of FIG. 2).

As shown in FIG. 1, puncture needle assembly 10 includes a needle cannula 30 disposed exteriorly on stylet 12 for slidably receiving stylet 12. Advantageously, the cannula sleeve is formed of stainless steel or from a biocompatible plastic tubing For a 19-gauge stylet, a cannular having an outer diameter of 0.042 inch and an inner diameter of 0.035 inch is suitable, whereas for an 18-gauge stylet, a cannula having an outer diameter of 0.05 inch and an inner diameter 0.042 inch is suitable.

Figure 4:
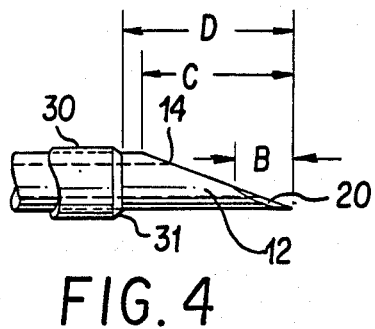
FIG. 4 is a detailed view, with portions broken away, of the tip portion of the distal end of a puncture needle assembly as shown in FIG. 1.
Figure 5:
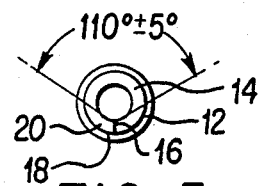
FIG. 5 is a detailed front elevational view of the distal end of the puncture needle assembly tip portion shown in FIG. 4.
Figure 6:
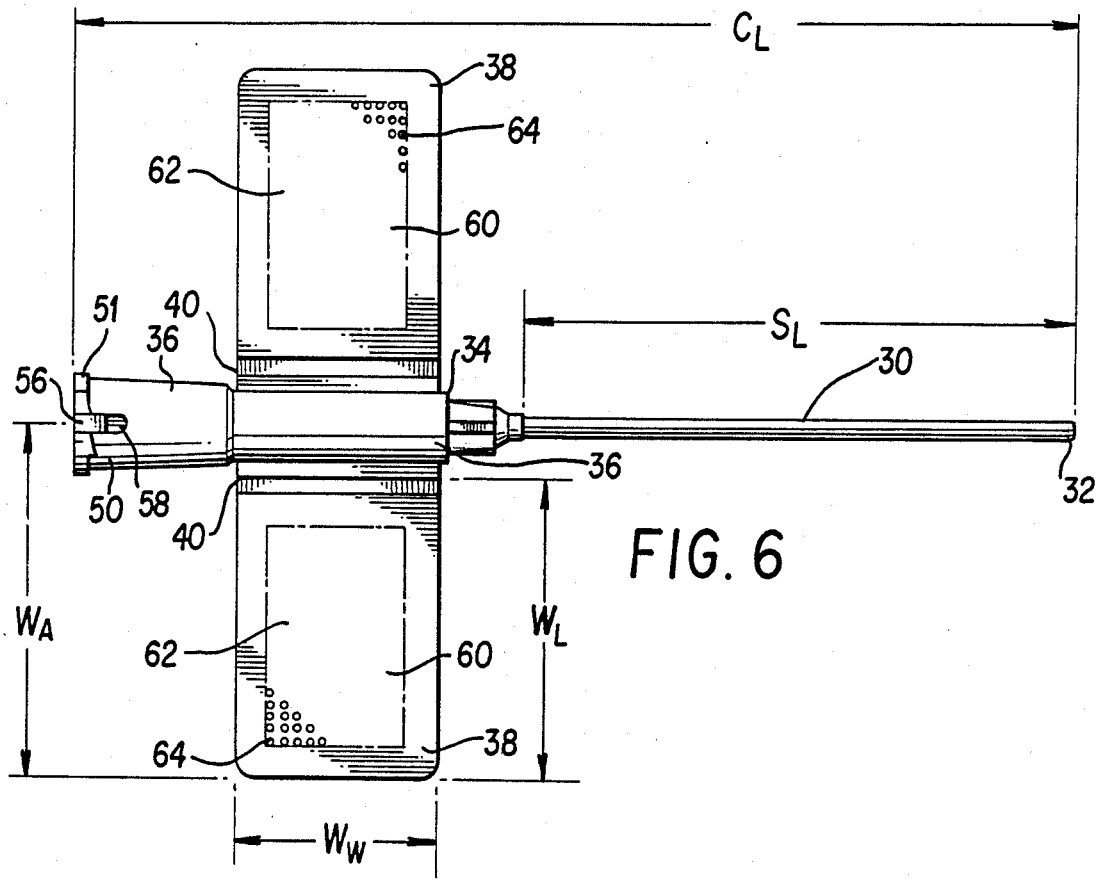
FIG. 6 is a top elevational view of the needle cannula of the puncture needle assembly shown in FIG. 1.

The cannular includes a distal end 32, and terminates at a proximal end thereof in a cannula hub 34 having a body portion 36. See FIGS. 1 and 6. To reduce the trauma of insertion, the cannula tip 31 is tapered as shown in FIG. 4, e.g., with a 0.015 inch by 0.001 inch bevel.

A pair of wings 38 extend outwardly from the cannula body portion 36, the wings having flexible hinge areas 40 adjacent the cannula body portion 36. See FIGS. 1, 6 and 7. As shown in FIGS. 1 and 8, the flexibl hinge area 40 allow wings 38 to fold towards each other about the cannula axis to grip the fin 26 extending from the stylet hub.

Figure 7:
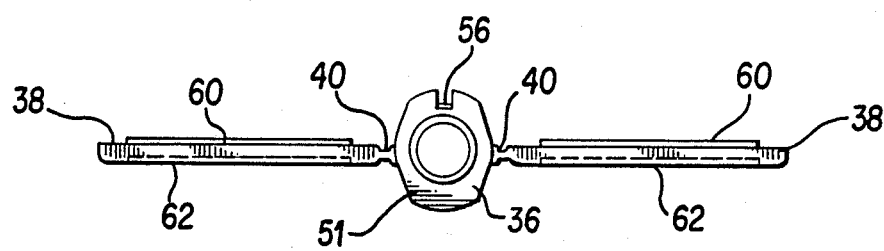
FIG. 7 is a rear elevational view of the needle cannula shown in FIG. 6.
Figure 8:
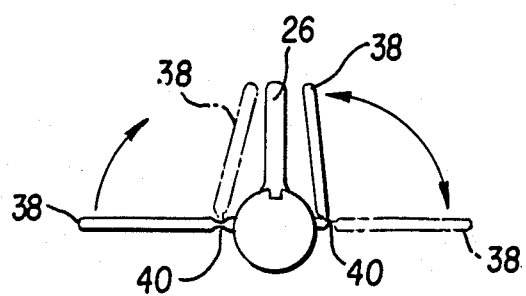
FIG. 8 is a rear elevational view of the puncture needle assembly shown in FIG. 1.

In preferred embodiments, the wings are connected perpendicularly to the hub by hinges 40 with the hinges on opposite sides of th4 cannular body portion with respect to the cannula axis, as shown clearly in FIG. 7. A rear connector portion 50 of the body portion 36 of the cannula hub extends a considerable distance from wings 38, for example, about 0.4 inch, terminating in a conventional "luer" lock hub portion 51 for connecting to a mating line connector. See FIGS. 6 and 7.

Means are provided for releasably interlocking the cannula hub and the stylet in position to prevent rotation of the stylet within the needle cannula. In the embodiment shown, this means for releasably interlocking the cannula hub and the stylet hub includes a locking tab 52 having a projecting end 54 fixedly connected to the stylet hub 22 between fin 26 and eyelet 12. See FIGS. 1, 2 and 3. The locking projection 52 of the stylet hub complementarily fits within a slot 56 in a cannula hub with locking projection 54 fitting within a complementary depression 58 along slot 56 thereby interacting the cannula hub with the stylet hub for releasably interlocking the cannula hub and the stylet hub in a locked position to prevent rotation of the stylet within the needle cannula. With the stylet hub and cannula hub interlocked, the beveled stylet distal end 14 extends beyond the cannula end 32, advantageously about 0.101 inch (dimension D in FIG. 4).

In the interlocked position, the stabilizer fin 26 is disposed between cannula wings 38, and positioned substantially equidistant from the hinge areas 40 of the cannula wings so that the stylet fin 26 can be gripped between the cannula wings 38 when folded towards each other substantially symmetrically with respect to the plane defined by the longitudinal axis of the stylet and the point of the beveled end of the stylet.

In preferred embodiments, the cannula sleeve length (dimension $S_L$ in FIG. 6) is from about 1 to about 2 inches, whereas the overall length of the cannula portion including the cannula hub (dimension $C_L$ in FIG. 6) is from about 2½ to about 3 inches. With a 19-gauge stylet, the preferred overall length is about 2.46–3.05 inches, and with an 18-gauge stylet, preferably from about 2.51 to about 3.10 inches. With a fin length of about 1-11/32 inches, a suitable wing width (dimension $W_W$ of FIG. 6) is about 0.508 inch, and a suitable wing length (dimension $W_L$ in FIG. 6) is about 0.594 inch with a wing tip to cannula axis length (dimension $W_A$ in FIG. 6) of about 0.75 inch.

Advantageously, the cannula hub and wing portion are formed of one-piece plastic with the finger-gripping portions 60 of wings 38 being rigid and considerably thicker than the bendable hinge portions 40 connecting wings 38 to the body portion of the cannula hub. The gripping surfaces 62 of wings 38 are provided with a plurality of gripping dots 64 that interact with complementary gripping dots 66 on the outer surfaces of each side of the stabilizer fin 26 to assist in preventing axial movement of the stylet within the cannula when the puncture needle is assembled and in use with the stylet fin gripped between wings 38.

If desired, the end portion of the stylet hub can include a hub cap 68 with a central opening 70 through which blood may pass for indicating proper placement of the puncture needle in a blood vessel. See FIG. 1.

The wings 38 of a puncture needle according to the present invention can be gripped by a thumb and one finger, with the stabilizing stylet fin 26 sandwiched therebetween. The wings 38 are displaced away from the back end of the needle so that the back end is clearly visible while the needle is being inserted into a blood vessel and the flow of blood can immediately be detected through the back end of the needle. Gripping by means of the thumb and forefinger engaging the wings allows more convenient holding of the needle than with prior art devices, and facilitates greater accuracy in inserting the needle assembly. Alignment of the stabilizer fin 26 with the plane defined by the longitudinal axis of the stylet and the point of the beveled end of the stylet enables a physician to known from the position of the stabilizer fin the exact location of the beveled distal end 14 of stylet 12 while it is being inserted into a blood vessel, without blockage from view by the physician's hand of the opening 70 at the end of the stylet through which the first dripping of blood from the blood vessel can be detected.

Since many modifications, variations and changes in detail may be made to the described embodiments, it is intended that all matter in the foregoing description and shown in the accompanying drawings be interpreted as illustrative and not in a limiting sense.

What is claimed is:

1. A puncture needle assembly, comprising:
   (a) a hollow, open-ended stylet through which liquid may pass, the stylet being beveled at a distal end to form a point on one side of the stylet, said stylet having a stylet hub assembly fixed about a proximal end of the stylet, the stylet hub assembly including a body portion and a stabilizer fin extending outwardly from the body portion to the stylet hub assembly, the fin extending in a plane defined by the longitudinal axis of the stylet and the point of the beveled end of the stylet, the fin extending radially from a side of the stylet that is opposite the side on which the stylet point is located, and
   (b) a needle cannula disposed exteriorly on the stylet for slidably receiving the stylet, the needle cannula including a sleeve portion with a distal end, and terminating at a proximal end thereof in a cannula hub having a body portion and including a pair of wings extending outwardly from the cannula body portion, the wings having flexible hinge areas adjacent the cannula body portion that allow the wings to fold towards each other about the cannula axis, the body portion of the cannula hub including means for interacting with the stylet hub for releasably interlocking the cannula hub and the stylet hub in a locked position to prevent rotation of the stylet within the needle cannula, in which locked position the beveled distal end of the stylet extends outside the distal end of the needle cannula and the stabilizer fin is disposed between the cannula wings and positioned substantially equidistant from the hinge areas of the cannula wings so that the stylet fin can be gripped between the cannula wings when folded towards each other substantially symmetrically with respect to said plane.

2. The puncture needle assembly of claim 1 wherein the proximal end of the stylet is spaced away from the hinged area of the cannula wings for providing visibility of liquid passing through the stylet and out an opening in the stylet at the proximal end thereof.

3. The puncture needle assembly of claim 1 wherein the stylet is 18 or 19 gauge hollow, surgical stainless steel needle tubing.

4. The puncture needle assembly of claim 1 wherein the overall bevel length of the beveled end of the stylet is about 0.086±0.009 inch.

5. The puncture needle assembly of claim 4 wherein the bevel includes a sharpened edge portion forming the tip of the stylet, the sharpened edge portion comprising 40-50% of the overall bevel length.

6. The puncture needle assembly of claim 5 wherein the bevel tip has an end-on bevel angle of about 110°±5°.

7. The puncture needle assembly of claim 1 wherein the fin has a longitudinal length parallel with the stylet axis of about 1-2 inches.

8. The puncture needle assembly of claim 1 wherein the fin extends about ½-1 inch outwardly from the axis of the stylet.

9. The puncture needle assembly of claim 1 wherein the fin extends about ¾ inch outwardly from the axis of the stylet.

10. The puncture needle assembly of claim 1 wherein the sleeve portion of the cannula is formed of stainless steel or biocompatible plastic tubing.

11. The puncture needle assembly of claim 10 wherein the distal end of the sleeve portion of the cannula is tapered to reduce trauma of insertion.

12. The puncture needle assembly of claim 3 wherein the stylet is 18 gauge and the cannula sleeve has an inner diameter of about 0.042 inch and an outer diameter of about 0.05 inch.

13. The puncture needle assembly of claim 3 wherein the stylet is 19 gauge and the cannula sleeve portion has an inner diameter of 0.035 inch and an outer diameter of 0.042 inch.

14. The puncture needle assembly of claim 1 wherein the cannula sleeve length is about 1-2 inches.

15. The puncture needle assembly of claim 3 wherein the overall length of the needle cannula including the sleeve portion and cannula hub portion is about 2½ to 3 inches.

16. A puncture needle assembly, comprising:
(a) a hollow, open-ended stylet through which liquid may pass, the stylet being beveled at a distal end to form a point on one side of the stylet, said stylet having a stylet hub assembly fixed about a proximal end of the stylet, the stylet hub assembly including a body portion and a stabilizer fin extending outwardly from the body portion to the stylet hub assembly, the fin extending in a plane defined by the longitudinal axis of the stylet and the point of the beveled end of the stylet, the fin extending radially from a side of the stylet that is opposite the side on which the stylet point is located, and
(b) a needle cannula disposed exteriorly on the stylet for slidably receiving the stylet, the needle cannula including a sleeve portion with a distal end, and terminating at a proximal end thereof in a cannula hub having a body portion and including a pair of wings extending outwardly from the cannula body portion, each wing being connected by a corresponding hinge to the cannula body portion on opposite sides thereof and perpendicularly thereto in a plane extending through the cannula axis, which hinges allow the wings to fold toward each other about the cannula axis, the body portion of the cannula hub including means for interacting with the stylet hub for releasably interlocking the cannula hub and the stylet hub in a locked position to prevent rotation of the stylet within the needle cannula, in which locked position the beveled distal end of the stylet extends outside the distal end of the needle cannula and the stabilizer fin is disposed between the cannula wings and positioned sustantially equidistant from the hinges of the cannula wings so that the stylet fin can be gripped between the cannula wings when folded toward each other substantially symmetrically with respect to said plane.

* * * * *